US006271210B1

(12) United States Patent
Sivaraman et al.

(10) Patent No.: US 6,271,210 B1
(45) Date of Patent: Aug. 7, 2001

(54) ANTISENSE OLIGONUCLEOTIDES FOR MITOGEN-ACTIVATED PROTEIN KINASES AS THERAPY FOR CANCER

(75) Inventors: Vimala S. Sivaraman; Hsien-yu Wang; Craig C. Malbon, all of Setauket, NY (US)

(73) Assignee: The Research Foundation of SUNY, Albany, NY (US)

( * ) Notice: Subject to any disclaimer, the term of this patent is extended or adjusted under 35 U.S.C. 154(b) by 0 days.

(21) Appl. No.: 09/412,289

(22) Filed: Oct. 5, 1999

Related U.S. Application Data

(63) Continuation of application No. 08/909,742, filed on Aug. 12, 1997, now Pat. No. 6,007,991, which is a continuation-in-part of application No. 08/831,994, filed on Apr. 1, 1997, now abandoned, which is a continuation-in-part of application No. 08/827,520, filed on Mar. 28, 1997, now abandoned.

(51) Int. Cl.[7] .......................... A61K 48/00; C07H 21/04; C12N 15/85; C12Q 1/68

(52) U.S. Cl. ..................... 514/44; 435/320.1; 435/325; 435/366; 536/24.5

(58) Field of Search ........................ 514/44; 435/6, 435/91.1, 320.1, 325, 366; 536/23.1, 245

(56) References Cited

U.S. PATENT DOCUMENTS

| 5,525,625 | 6/1996 | Bridges et al. ........................ 514/456 |
|---|---|---|
| 5,582,986 | 12/1996 | Monia et al. .............................. 435/6 |
| 5,593,884 | 1/1997 | Karin et al. ......................... 475/252.3 |
| 5,597,719 | 1/1997 | Freed et al. ............................ 435/194 |
| 6,007,991 | * 12/1999 | Sivaraman et al. ....................... 435/6 |

FOREIGN PATENT DOCUMENTS

WO 91/19008   12/1991  (WO) .

OTHER PUBLICATIONS

Branch, A good antisense molecule is hard to find, TIBS, vol. 23, pp. 45–50, Feb. 1998.*
Agrawal, Antisense oligonucleotides:towards clinical trials, TIBTECH, vol. 14, pp. 376–387, Oct. 1996.*
Gewirtz et al., Facilitating oligonucleotide delivery: helping antisense deliver on its promise, PNAS, vol. 93, pp. 3161–3163, Apr. 1996.*
Antisense '97: A roundtable on the state of the industry, Nature Biotechnology, vol. 15, pp. 519–524, Feb. 1998.*
Ito, et al., "Activation on Mitogen–Activated Protein Kinases Extracellular Signal–Regulated Kinases in Human Hepatocellular Carcinoma", *Hepatology*, 27: (4), pp. 951–958 (1998).
Coutts, et al., "Elevated Mitogen–Activated Protein Kinase Activity in Estrogen–Nonresponsive Human Breast Cancer Cells", *Cancer Research*, 58: (18), pp. 4071–4074 (1998).

Bang, et al., "Increased MAPK Activity and MKP–1 Overexpression in Human Gastric Adenocarcinoma", *Biochemical and Biophysical Research Communications*, 250: (1), pp. 43–47 (1998).
Nishio, et al., "Mitogen–Activated Protein Kinase Antisense Oligonucleotide Inhibits The Growth of Human Lung Cancer Cells", *International Journal of Oncology*, 14: (3), pp. 461–469 (1999).
Reddy, et al., "Mitogen–Activated Protein Kinase (MAPK) Regulates the Expression of Progelatinase B (MMP–9) in Breast Epithelial Cells", *International Journal of Cancer*, 82: (2), pp. 268–273 (1999).
Salh, et al., "Investigation of the Mek–MAP Kinase–Rsk Pathways in Human Breast Cancer", *Anticancer Research*, 19: (1B), pp. 731–740 (1999).
Sebolt–Leopold, et al., "Blockade of the MAP Kinase Pathway Suppresses Growth of Colon Tumors In Vivo", *Nature Medicine*, 5: (7), pp. 810–816 (1999).
Price, et al., "Activation of Extracellular Signal–Regulated Kinase in Human Prostate Cancer", *Journal of Urology*, 162: (4), pp. 1537–1542 (1999).
Wang, et al., "Mammary Cancer Promotion and MAPK Activation Associated with Consumption of a Corn Oil–Based High–Fat Diet", *Nutrition and Cancer–An International Journal*, 34: (2), pp. 140–146 (1999).
Toyoda, et al., "Increased Activity and Expression of MAP Kinase in HCC Model Rats Induced by 3'–Methyl–4–Dimethylamino–Azobenzene", *Journal of Hepatology*, 31: (4), pp. 725–733 (1999).
Park, et al., "Differential Regulation of MAP Kinase Cascade in Human Colorectal Tumorigenesis", *British Journal of Cancer*, 81: (7), pp. 1116–1121 (1999).
Maemura, et al., "Mitogen–Activated Protein Kinase Cascade in Breast Cancer", *Oncology*, 57: pp. 37–44, Suppl. 2 (1999).
Galvin–Parton et al., "In Vivo Analysis of Signaling Elements via Targeted, Inducible Antisense RNA", *Methods in Molecular Genetics* 8 362–372 (1996).
Gao et al., "Morphogen–Induced Decline in $G_{1\alpha2}$ Triggers F9 Teratocarcinoma Stem Cell Progression Via Phospholipase C and Mitogen–Activated Protein Kinase", *The Journal of Biological Chemistry* 271 9002–9008 (1996).
Brunet et al., "Le Module MAP Kinase: Rôle Dans Le Contrôle De La Prolifération Cellulaire", *C. R. Soc. Biol.* 189 43–57 (1995) (English Abstract).

(List continued on next page.)

*Primary Examiner*—Andrew Wang
(74) *Attorney, Agent, or Firm*—Hoffman & Baron, LLP

(57) ABSTRACT

A method is disclosed for inhibiting malignant neoplastic growth of epithelial or endothelial cells in a mammal by administering to the mammal an effective amount of an oligonucleotide complementary to at least a portion of mRNA for ERK-1 or ERK-2 that is overexpressed in the mammal. The antisense oligonucleotides are administered to the mammal as a dosage unit. A method of identifying and monitoring potentially malignant neoplastic cell growth in a mammal is also disclosed.

6 Claims, 10 Drawing Sheets-

OTHER PUBLICATIONS

Sale et al., "Requirement of MAP Kinase for differentiation of Fibroblasts to Adipocytes, for Insulin Activation of p90 S6 Kinase and for Insulin of Serum Stimulation of DNA Synthesis", *The EMBO Journal* 14 674–684 (1995).

Hunter, "Protein Kinases and Phosphatases: The Yin and Yang of Protein Phosphorylation and Signaling", *Cell* 80 225–236 (1995).

Cobb et al., "How MAP Kinases Are Regulated" *The Journal of Biological Chemistry* 270 14843–14846 (1995).

Nuovo et al., "Correlation of the in Situ Detection of Polymerase Chain Reaction–Amplifie Metalloproteinase Complementary DNAs and Their Inhibitors with Prognosis in Cervical Carcinoma", *Cancer Research* 55 267–273 (1995).

Cobb, "The Role of the MAP Kinase Pathway in Breast Cancer", National Technical Information Service, Accession No. AB–8301 655/7/XAB (1995).

Stull et al., "Antigene, Ribozyme and Aptamer Nucleic Acid Drugs: Progress and Prospects", *Pharmaceutical* 12 465–483 (1995).

Mansour et al., "Transformation of mammalian Cells by Constitutively Active MAP Kinas Kinase", *Science* 265 966–970 (1994).

Graff, "Messenger RNA Translation and Malignancy: The MRNA CAP–Binding Protein, EIF–4E, as an Integral Component of Malignancy in Cloned Rat", Dissertation, Chapter 6, 110–130 (1994).

Frost et al., "A Requirement for Extracellular Signal–Regulated Kinase (ERK) Function in the Activation of AP–1 by Ha–Ras, Phorbol 12–Myristate 12–Acetate, and Serum", *Proc. Natl. Acad. Sci. USA* 91 3844–3848 (1994).

Frost et al., "Simian Virus 40 Small t Antigen Cooperates with Mitogen–Activated Kinases to Stimulate AP–1 Activity", *Molecular and Cellular Biology* 14 6244–6252 (1994).

Voyno–Yasenetskaya et al., "Mutant α subunits of G12 and G13 Proteins Induce Neoplastic Transformation of Rat–1 Fibroblasts", *Oncogene* 9 2559–2565 (1994).

Brunet et al., "Constitutively Active Mutants of MAP Kinase Kinase (MEK) Induce Growth–Factor–Relaxation and Oncogenicity When Expressed in Fibroblasts", *Oncogene* 9 3379–3387 (1994).

Janes et al., "Activation of the Ras Signaling Pathway in Human Breast Cancer Cells Overexpressing erB–2", *Oncogene* 9 3601–3608 (1994).

Mansour et al., "Transformation of Mammalian Cells by Constitutively Active MAP Kinas Kinase", *Science* 265 966–970 (1994).

Robbins et al., "Map Kinases ERK1 and ERK2: Pleiotropic Enzymes in a Ubiquitous Signaling Network", *Advances in Cancer Research* 63 93–117 (1994).

Moxham et al., "Induction of $G\alpha_{i2}$–Specific Antisense RNA In Vitro Inhibits Neonatal Growth", *Science Series* 260 991–995 (1993).

Lippman, "The Development of Biological Therapies for Breast Cancer", *Science* 259 631–632 (1993).

Sontag, "The Interaction of SV40 Small Tumor Antigen with Protein Phosphatase 2A Stimulates the Map Kinase Pathway and Induces Cell Proliferation", *Cell* 75 887–897 (1993).

Blenis, "Signal Transduction Via the MAP Kinases: Proceed at Your Own RSK" *Proc. Natl. Acad. Sci. USA* 90 5889–5892 (1993).

Nuovo et al., "In Situ Detection of PCR–Amplified HIV–1 Nucleic Acids and Tumor necrosis Factor cDNA in Cervical Tissues", *American Journal of Pathology* 143 40–48 (1993).

Gupta et al., "Map Kinase is Constitutively Activated in gip2 and src Transformed Rat HeLa Cells", *The Journal of Biological Chemistry* 267 7987–7990 (1992).

Allred et al., "Overexpression of HER–2/new and Its Relationship with Other Prognostic Factors Change During the Progression of In Situ to Invasive Breast Cancer", *Human Pathology* 23 974–979 (1992).

Wang et al., "Antisense Oligodeoxynucleotides to $G_s$ Proteinα–subunit Sequence Accelerate Differentiation of Fibroblasts to Adipocytes" *Nature* 358 334–337 (1992).

Kobayashi et al., "Estrogen Receptor, c–erbB–2 and nm23/NDP Kinase Expression in the Intraductal and Invasive Components of Human Breast Cancers", *Jpn. J. Cancer Res.* 83 859–865 (1992).

Allred et al., "HER–2/neu in Node–Negative Breast Cancer: Prognostic Significance of Overexpression Influenced by the Presence of In situ Carcinoma", *Journal of Clinical Oncology* 10 599–605 (1992).

Trojan et al., "Loss of Tumorigenicity of Rat Glioblastoma Directed by Episome–Based Antisense cDNA Transcription of Insulin–Like Growth Factor I", *Proc. Natl. Acad. Sci. USA* 89 4874–4878 (1992).

Seger et al., "Purification and Characterization of Mitogen–Activated Protein Kinase Activator(s) from Epidermal Growth Factor–Stimulated A431 Cells", *The Journal of Biological Chemistry* 267 14373–14381 (1992).

Boulton et al, "Identification of Multiple Extracellular Signal–Regulated Kinases (ERKs) with Antipeptide Antibodies", *Cell Regulation* 2 357–371 (1991).

Arteaga et al., "Elevated Content of the Tyrosine Kinase Substrate Phospholipase C–γ1 in Primary Human Breast Carcinomas", *Proc. Natl. Acad. Sci. USA* 88 10435–10439 (1991).

Maguire et al., "Neu(c–erbB–2), a Tumor Marker in Carcinoma of the Female Breast", *Pathobiology* 58 297–303 (1990).

Maguire, Jr. et al., "Neu (c–erbB–2), a Tumor Marker in Carcinoma of the Female Breast", *Pathobiology* 58 297–303 (1990).

Slamon et al., "Studies of the HER–2/neu Proto–oncogene in Human Breast and Ovarian Cancer" *Science* 244 707–712 (1989).

Anfossi et al., "An Oligomer Complementary to c–myb–encoded mRNA Inhibits Proliferation of Human Myeloid Leukemia Cell Lines", *Proc. Natl. Acad. Sci. USA* 86 3379–3383 (1989).

Hudziak, "Amplified Expression of the HER2/ERBB2 Oncogene Induces Resistance to Tumor Necrosis Factor α in NIH 3T3 Cells", *Proc. Natl. Acad. Sci. USA* 85 5102–5106 (1988).

Muller et al., "Single–Step Induction of Mammary Adenocarcinoma in Transgenic Mice Bearing the Activated c–neu Oncogene", *Cell* 54 105–115 (1988).

"Amplification of c–erbB–2 and Aggressive Human Breast Tumor?", *Science* 240 1795–1798 (1988).

Wickstrom, "Human Promyelocytic Leukemia HL–60 Cell Proliferation and c–myc Protein Expression are Inhibited by an Antisense Pentadecadeoxynucleotide Targeted Against c–myc mRNA", *Proc. Natl. Acad. Sci. USA* 85 1028–1032 (1988).

Holt et al., "An Oligomer Complementary to c–myc mRNA Inhibits Proliferation of HL–60 Promyelocytic Cells and Induces Differentiation", *Molecular and Cellular Biology* 8 963–973 (1988).

Slamon, "Human Breast Cancer: Correlation of Relapse and Survival with Amplification of the HER–2/neu Oncogene", *Science* 235 177–235 (1987).

Di Fiore et al., "erbB–2 Is a Potent Oncogene When Over-expressed in NIH/3T3 Cells" *Science* 237 178–182 (1987).

Hudziak et al., "Increased Expression of the Putative Growth Factor Receptor $p185^{HER2}$ Causes Transformation and Tumorigenesis of NIH 3T3 Cells", *Proc. Natl. Acad. Sci, USA* 84 7159–7163 (1987).

Moxham, et al., "Mammalian β1– and β2– Adrenergic Receptors", *The Journal of Biological Chemistry*, 261 14562–14570 (1986).

* cited by examiner

FIG-3A  EOSIN + HEMATOXYLIN STAIN
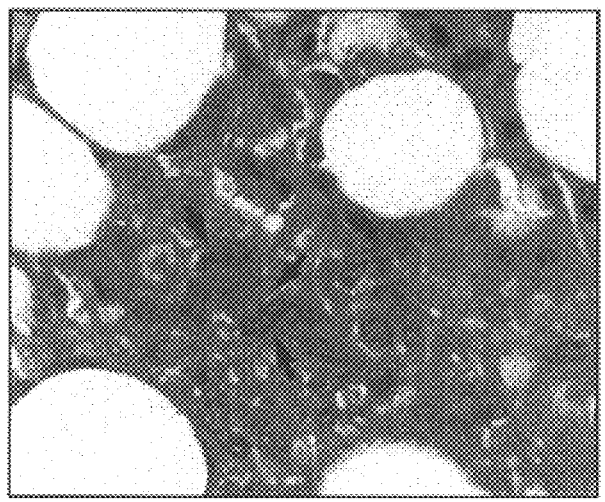
FIG-3B  NEGATIVE CONTROL IN SITU RT-PCR
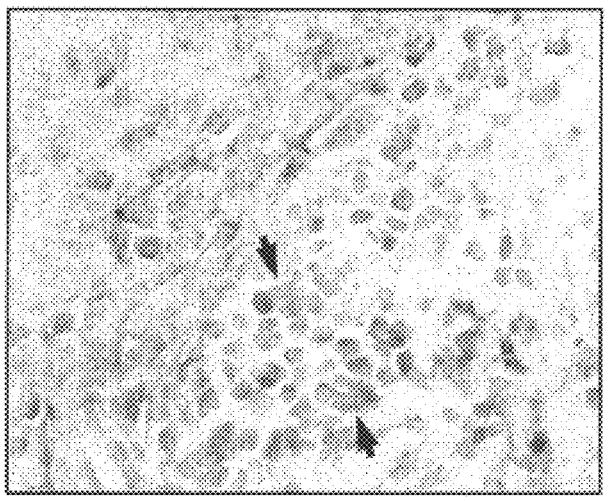

FIG-3C  POSITIVE CONTROL (-DNASE)
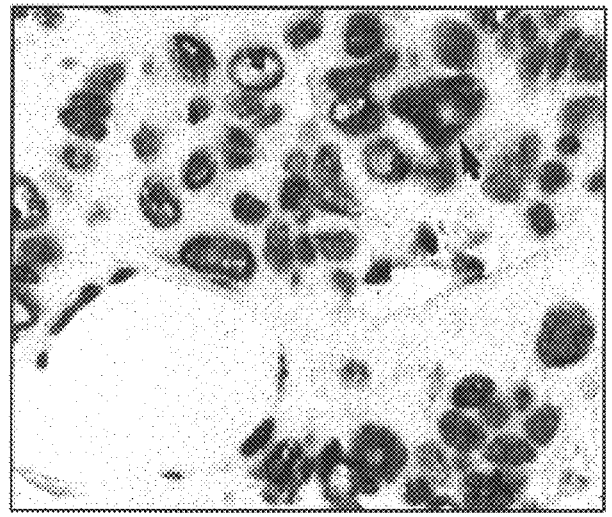
FIG-3D  PATIENT DW IN SITU RT-PCR

FIG-3E  PATIENT DW *IN SITU* RT-PCR
FIG-3F  PATIENT DW *IN SITU* RT-PCR

FIG-4A  EOSIN + HEMATOXYLIN STAIN
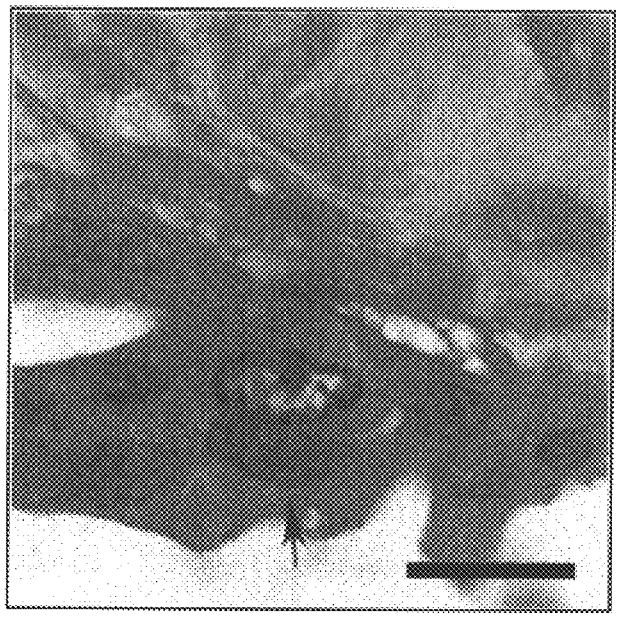
FIG-4B  NEGATIVE CONTROL *IN SITU* RT-PCR
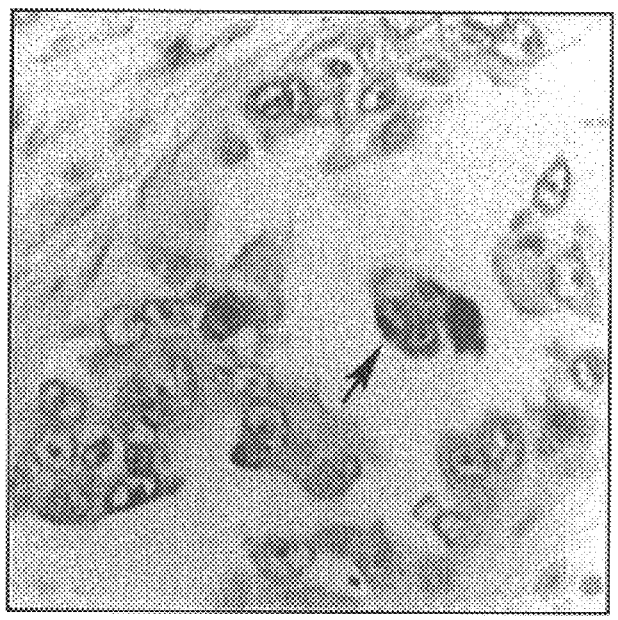

FIG-4C  POSITIVE CONTROL (-DNASE)
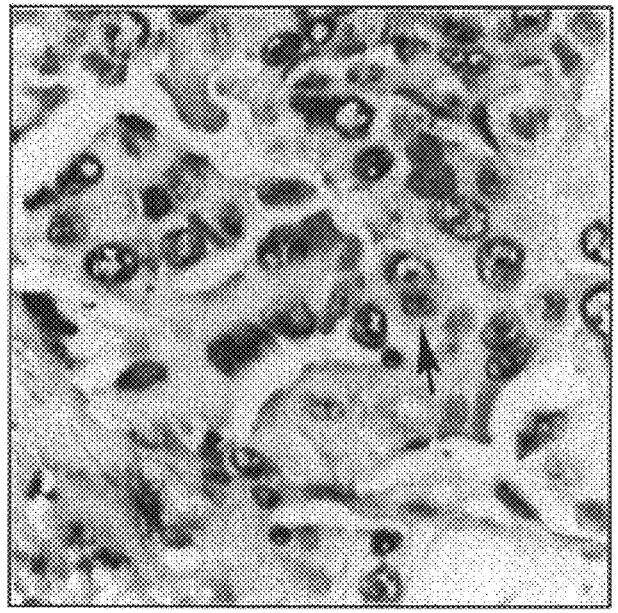
FIG-4D  IN SITU RT-PCR
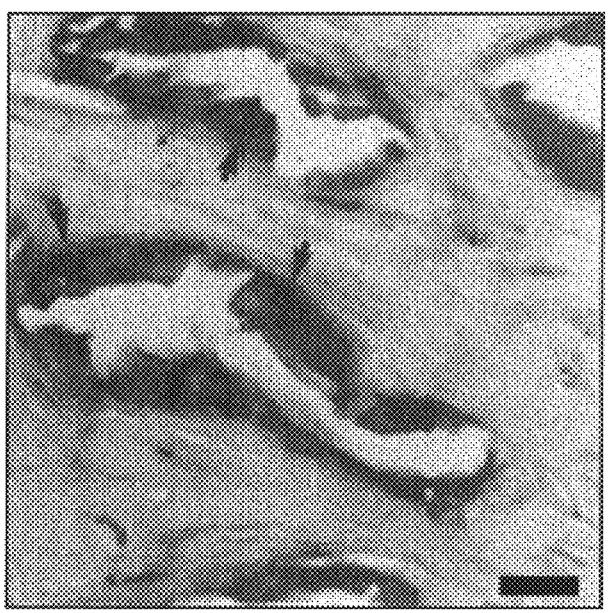

FIG-5A  PRIMARY BREAST CANCER
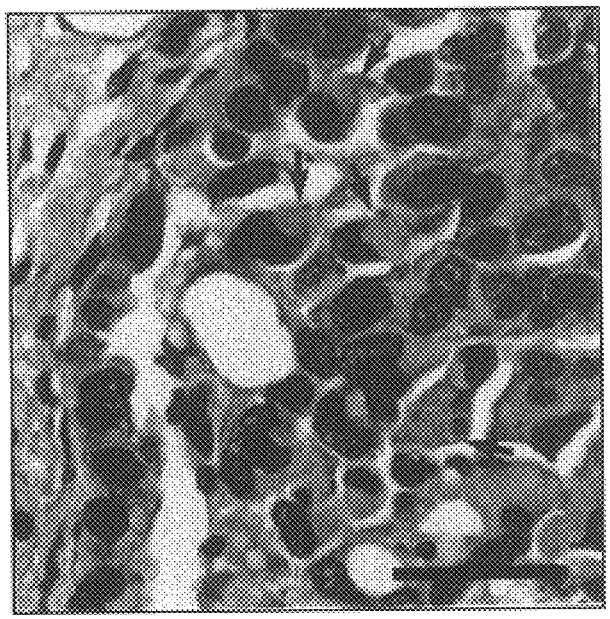
FIG-5B  INVOLVED LYMPH NODE
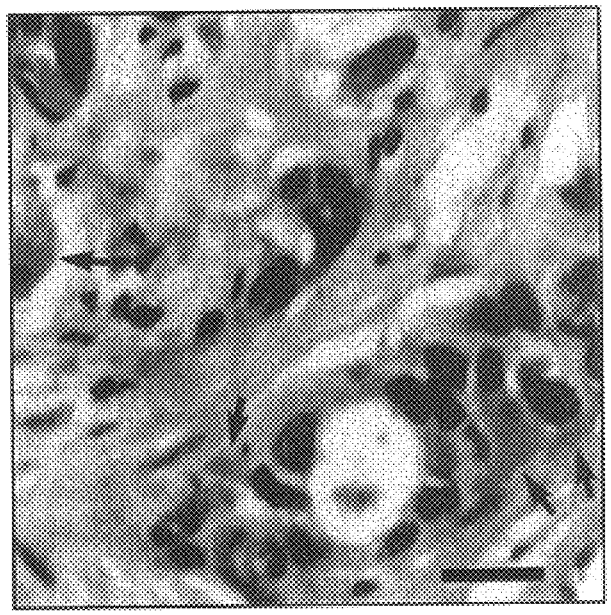

IB:α MAPK

IP:α MAPK
IB:α PY

IB:α ACTIVE - MAPK

ANTISENSE OLIGONUCLEOTIDES FOR MITOGEN-ACTIVATED PROTEIN KINASES AS THERAPY FOR CANCER

This application is a continuation of U.S. Ser. No. 08/909,742, filed on Aug. 12, 1997, now U.S. Pat. No. 6,007,991, which is a Continuation-in-Part of U.S. Ser. No. 08/831,994, filed Apr. 1, 1997, now abandoned, which is a Continuation-in-Part of U.S. Ser. No. 08/827,520, filed on Mar. 28, 1997 now abandoned.

This invention was made with private support under Grant No. BE 188 sponsored by the American Cancer Society.

This invention was made with government support under Grant No. DK 30 111, awarded by the National Institute of Health. The government has certain rights in this invention.

FIELD OF THE INVENTION

The invention relates to a method of treating cancer In a mammal, and more particularly to the treatment of cancer in a mammal with antisense oligonucleotides.

BACKGROUND OF THE INVENTION

Cancer is generally a disease of the intracellular signaling system. Normal cells respond to many extracellular signals by proliferating, differentiating or otherwise altering their metabolic activity. Such signals are received at the cell surface and converted by a system of signal transduction proteins into a message decipherable by the cell. The message is responsible for subsequent regulation of cell processes.

An example of proteins that are involved in the signal transduction pathway are the mitogen-activated protein (MAP) kinases. The MAP kinases are believed to be directly involved in the regulation of genes that are responsible for cell proliferation.

The MAP kinase superfamily of genes includes three families. One of these families includes the genes that encode ERK-1 and ERK-2. The second family includes the genes that encode the stress activated protein kinases, such as JUN kinase The third family includes the gene that encodes p38.

The MAP kinases, in turn, are regulated by various levels of upstream regulatory proteins. The mechanism of regulation of MAP kinases is reversible protein phosphorylation.

The first level of upstream MAP kinase regulatory proteins includes the family of MAP kinase kinases, such as MEK. The MAP kinase kinases, in turn, are regulated by the second level of regulatory proteins, the MAP kinase kinase kinases.

It is believed that cancer is commonly caused by defects in the genes responsible for signal transduction. Such defective genes are called oncogenes. Oncogenes can lead to the overexpression of one or more signal transduction proteins causing the cell nucleus to receive an inappropriate signal to proliferate. Defective signals can occur through a variety of mechanisms.

The proteins expressed by oncogenes, called oncoproteins, typically act directly as transactivators and regulators of the synthesis of RNA and DNA. Many oncogenes are members of the family of MAP kinase kinases and MAP kinase kinase kinases. Some examples of oncogenes that have been widely studied are ras, raf-1, myc, ski, myb, fos and jun. See Blenis, J. "Signal Transduction Via MAP Kinase: Proceed at Your Own Risk," *Proc. Natl. Acad. Sci. U.S.A.*, Vol. 90, 5889–5892 (1994); Cobb, et al., "How MAP Kinases Are Regulated," *J. Biol. Chem.*, Vol. 270, 14843–14846 (1995), and Janes, et al., "Activation of the Ras Pathway In Breast Cancer Cells," *Oncogene*, Vol. 9, 3601–3608 (1994).

For example, constitutively active MAP kinases are believed to induce oncogenicity when a MAP kinase kinase (MEK) is expressed in fibroblasts. Brunet e al., "MAP Kinase Module: Role in the Control of Cell Proliferation," *Comptes. Rendus. Sci. Soc. Biol.*, Vol. 189, 43–57 (1995); Brunet et al., "Constitutively Active Mutants of MAP Kinase Induced Growth Factor-Relaxation and Oncogenicity When Expressed in Fibroblasts," *Oncogene*, Vol. 9, 3379–3387 (1994).

A number of viral and cellular genes have been identified as potential oncogenes. The products of oncogenes are classified according to their cellular location, for example, secreted, surface, cytoplasmic, and nuclear oncoproteins.

The products of nuclear oncogenes have the ability to induce alterations in gene regulation leading to abnormal cell growth and ultimately neoplasia. As a result of the expressed products of oncogenes being involved in the formation of potentially malignant neoplastic cell growth, there has been much focus on methods of inhibiting oncoprotein expression.

A technique that is becoming prevalent to inhibit expression of a target protein, such as an oncoprotein, is the use of antisense oligonucleotides. Antisense oligonucleotide inhibition of oncogenes has proven to be a useful tool in understanding the roles of the various oncogene families.

Antisense oligonucleotides are small oligonucleotides that are complementary to, and thus able to specifically hybridize with, the mRNA transcript of the target gene. In some instances, the antisense oligonucleotides bind to the major groove of the double stranded (ds) DNA that encodes the target protein to form a triple helix or antigene. Binding to either the mRNA or the dsDNA inhibits expression of the targeted protein. A discussion of such triple helixes is found in Stull et al., "Antigene, Ribozyme and Aptamer Nucleic Acid Drugs: Progress and Prospects," *Pharm. Res.*, Vol. 14, No. 4, 465–483 (1995), incorporated herein by reference.

Considerable attention has been directed to how the expressed products of oncogenes alter the signal transduction pathway of cells. Currently, the focus on signal transduction pathway alterations is primarily directed to the upstream regulators of MAP kinases, such as ras, raf-1, and MEK. Some examples of this approach can be found in U.S. Pat. No. 5,582,986, which discloses antisense oligonucleotides for inhibition of the ras gene, U.S. Pat. No. 5,597,719, which discloses human 14-3-3 proteins that modulate raf-1 activity, and U.S. Pat. No. 5,525,625, which discloses flavone compounds that inhibit the activity of MEK.

In addition, Holt et al., *Mol. Cell Biol.*, Vol. 8, 963–973 (1988), have shown that antisense oligonucleotides hybridizing specifically with mRNA transcripts of the oncogene c-myc, when added to cultured HL60 leukemic cells, inhibit proliferation and induce differentiation. Anfossi et al., *Proc. Natl. Acad. Sci.*, Vol. 86, 3379–3383 (1989), have shown that antisense oligonucleotides specifically hybridizing with mRNA transcripts of the c-myb oncogene inhibit proliferation of human myeloid leukemia cell lines. Wickstrom et al., *Proc. Nat. Acad. Sci.*, Vol. 85, 1028–1032 (1988), have shown that expression of the protein product of the c-myc oncogene as well as proliferation of HL60 cultured leukemic cells are inhibited by antisense oligonucleotides hybridizing specifically with c-myc mRNA.

However, these strategies of inhibiting or inactivating the upstream regulators of MAP kinase, such as ras, raf-1 and MEK, have generally not been effective. It is becoming apparent that the proliferation pathway blocked by the inhibition may be replaced by other pathways that promote unregulated cell proliferation. The replacement pathway may occur in the malignant cells treated with the antisense oligonucleotides, or in clones of other malignant cells that co-exist with the treated cells.

In addition to the inhibition of the upstream regulators of MAP kinase discussed above, the inhibition of expression of MAP kinase itself has been demonstrated in vitro and in vivo. Such inhibition has, to date, been used mainly as a general research tool.

For example, Sale et al., disclose the use of antisense oligonucleotides to investigate the role of MAP kinase in the differentiation of fibroblasts to adipocytes, for insulin activation of p90 S6 kinase and for insulin or serum stimulation of DNA synthesis," Sale et al., *EMBO J.,* Vol. 14, No. 4, 674–684 (1995). Gao et al., disclose the use of the antisense oligonucleotides of Sale et al., to investigate the role of MAP kinase in F9 teratocarcinoma stem cell progression. Gao et al., *J. Biol. Chem.,* Vol. 271, No. 15, 9002–9008 (1996).

The role of MAP kinases in cancer has been investigated. These findings however, have been inconclusive, and have not provided new routes of inhibiting malignant neoplastic cell growth.

For example, it has been reported that the activity of MAP kinases ERK-1 and ERK-2 can be correlated to the overexpression of eIF-4E in CREF cells and the malignancy of each cell line. Graff, Jeremy R., "Messenger on a Translation and to Malignancy," The mRNA Cap-Binding Protein, eIF-4E, as an Integral Component of Malignancy in Cloned Rat, *Dissertation submitted to University of Kentucky,* Chapter 6, 110–130 (1994). However, no hypothesis as to the role of MAP kinase in cancer was made. Moreover, studies that illustrate the hyperactivation of MAP kinase do not provide any suggestions as to the cause of the hyperactivation. These findings do not provide new routes of treating malignant neoplastic cell growth, such as primary breast carcinoma.

Likewise, there has been a report of increased MAP kinase expression in cultured non-small cell lung carcinomas and breast cancer cell lines. However, only about a third of the breast cancer cell lines examined exhibited changes in MAP kinase expression. An inconsistent pattern was observed in which some cell lines exhibited more ERK-1 and others exhibited more ERK-2. Cobb, Melanie H., "The Role of MAP Kinase Pathway in Breast Cancer," *National Technical Information Service,* Accession No. AD-8301 655/7/XAB (1995). As a result of the se inconsistent findings, the author stated that she was unable to make even an initial hypothesis as to the role of MAP kinase in cancer. Another difficulty with this study, and other studies with cultured cell fines, is that one cannot extrapolate the results with the results obtained with non-cultured cells from biopsies.

At the present time, treatment of cancer primarily relies on the use of radiation and/or chemotherapeutic agents, such as vinblastine or adriamycin. However, it is widely recognized that the side effects of such treatments are at times severe, making these treatment strategies very unpopular.

Another problem related to cancer is the reliance on gross pathology to make an initial prognosis of malignant neoplastic cell growth. In many malignant neoplastic cell growths, early detection is difficult unless there is a phenotypical alteration to indicate malignancy. While there has been some progess in the development of assays for the detection of cancer in the early stages (e.g., prostate and melanoma), such assays are not applicable to other cancers, such as breast cancer.

In view of the above, it is apparent that there is a continuing need in the art for an effective treatment for cancer that removes the necessity of the administration of radiation and chemotherapeutic agents. Likewise, there is a continuing need in the art for a method of identifying and monitoring potentially malignant neoplastic growths which would allow for early detection and staging of the malignancy.

Accordingly, it is the object of the present invention to provide more effective methods that overcome the disadvantages of the prior art methods for identifying and monitoring potentially malignant neoplastic cell growth, and for treating cancer.

SUMMARY OF THE INVENTION

These and other objects which will be apparent to the skilled artisan, are accomplished by the present invention which is set forth below. In one embodiment, the invention relates to a method of inhibiting malignant neoplastic growth of epithelial or endothelial cells in a mammal, by administering to the mammal an effective amount of an oligonucleotide complementary to at least a portion of the mRNA for ERK-1, ERK-2, or both, that is overexpressed in the mammal. Preferably, the complementary oligonucleotide has about 10 to about 100, more preferably has about 15 to about 45, and even more preferably has about 17 to about 32 nucleotides. A particularly suitable oligonucleotide is selected from the group consisting of 5'-GCC GCC GCC GCC GCC AU-3', 5'-GCC GCC GCC GCC GCC AT-3' and mixtures thereof.

The oligonucleotide is preferably administered by injecting an effective amount of the oligonucleotide. For example, the injecting step is preferably accomplished by injecting the effective amount of the oligonucleotide at the site of the malignant neoplastic cell growth. The oligonucleotide can also be administered in an expression vector. Preferably, the expression vector is targeted to the malignant neoplastic cell growth in the mammal.

In another embodiment, the present invention relates to a dosage unit for administering antisense nucleotides to a mammal. Optimally, the oligonucleotide for the dosage unit is contained in a syringe.

In a third embodiment, the invention relates to a method of identifying and monitoring potentially malignant neoplastic cell growth in a mammal. The method includes the steps of (a) determining the level of expression of ERK-1, ERK-2, or both in epithelial or endothelial cells suspected of malignant neoplastic growth obtained from the mammal, and (b) ascertaining whether said level of expression determined in step (a) is higher than the level of expression of ERK-1, ERK-2, or both, in normal cells of identical origin. Preferably, the cells are obtained from the breast tissue of the mammal. A mammal particularly suitable for use with the invention is a human.

BRIEF DESCRIPTION OF TIE DRAWINGS

FIG. 3; panels A–F, are photomicrographs of epithelial cells of patients having benign growths and malignant growths (primary breast carcinoma) analyzed by in situ reverse transcriptase polymerase chain reaction (RT-PCR) for MAP kinase mRNA. Panel A shows epithelial cells having invasive cancer cells which exhibit high levels of MAP kinase mRNA, as indicated with arrows. Panel B shows a negative control of epithelial cells analyzed with PCR primers for an unrelated hepatitis C viral RNA after DNAse digestion. Panel C shows a positive control of epithelial cells analyzed with PCR primers for MAP kinase and genomic DNA, without DNAse pre-treatment. Panel D shows epithelial cells analyzed with PCR primers for MAP kinase, after pre-treatment with DNAse. Panels E and F show epithelial cells of one patient (DW) having both benign and malignant growths, respectively, analyzed by in situ RT-PCR.

FIG. 4, panels A–D, are photomicrographs of lymph node tissue exhibiting metastasized primary breast carcinoma subjected to in situ RT-PCR. Panel A shows lymph node tissue having metastatic cancer cells, which exhibit high levels of MAP kinase mRNA, as indicated with arrows. Panel B shows a negative control of lymph node tissue analyzed with PCR primers for an unrelated hepatitis C viral RNA after DNAse digestion. Panel C shows a positive control of lymph node tissue analyzed with PCR primers for MAP kinase and genomic DNA, without DNAse pre-treatment. Panel D shows lymph node tissue analyzed with PCR primers for MAP kinase, after pre-treatment with DNAase.

FIG. 5, panel A and B, are photomicrographs of primary breast cancer and lymph node tissue exhibiting metastasized primary breast cancer that have been subjected to immunohistochemical analysis to determine MAP kinase overexpression. Panel A shows the primary breast cancer immunecomplexed with a primary antibody to MAP kinase and stained with eosin and hematoxylin. Panel B shows the lymph node tissue immunecomplexed with a primary antibody to MAP kinase and stained with eosin and hematoxylin.

Figure 6A:
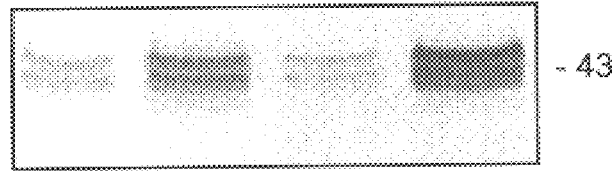
Figure 6B:
Figure 6C:
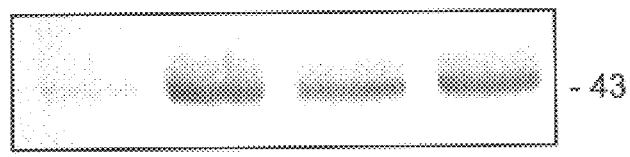

FIG. 6, panels A–C, are photographs of nitrocellulose blots of MAP kinase isolated from primary breast cancer tissue samples. Panel A shows MAP kinase isolated from tissue extract that has been subjected to SDS-polyacrylamide gel electrophoresis and immunoblot staining with a murine monoclonal anti-MAP kinase antibody. Panel B shows MAP kinase isolated from tissue extract that has been subjected to immunoprecipitation with a rabbit polyclonal anti-MAP kinase antisera (IP), followed by SDS-PAGE and immunoblot staining with an anti-phosphotyrosine antibody (IB). Panel C shows MAP kinase isolated from tissue extract that has been to subjected immunoblot staining with a rabbit polyclonal antibody specific for the dually phosphorylated (serine and tyrosine), "active" form of MAP kinase.

Figure 7:
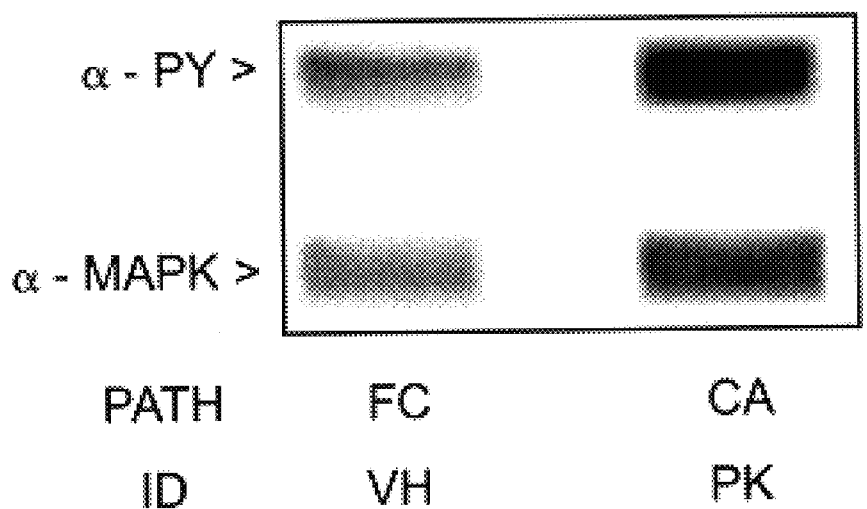

FIG. 7 is a photograph of a nitrocellulose blot of MAP kinase isolated from whole-cell extracts of primary breast carcinoma that has been subjected to SDS-PAGE and immunoblot stained with antibodies against either MAP kinase (MAPK) or phosphotyrosine (PY).

DETAILED DESCRIPTION OF THE INVENTION

It is now been discovered that the growth of malignant neoplastic cells of epithelial and endothelial origin can be inhibited by inhibiting the overexpression of the MAP kinases, ERK-1 and ERK-2. Examples of these epithelial and endothelial malignancies include, but are not limited to, primary or metastatic cancers of the breast, prostate, and other endocrine tissues as well as angiosarcoma, an endothelial cell-based cancer that may be found in any endothelial tissue, such as the vasculature.

As a result of this discovery, a method of inhibiting malignant neoplastic cell growth has been developed. In accordance with the present invention an oligonucleotide complementary to at least one portion of a targeted mRNA of either ERK-1, ERK-2, or both, is administered to a mammal. The amount administered should be effective to decrease the overexpression of ERK-1 or ERK-2 thereby inhibiting the malignant neoplastic cell growth found in the mammal. The level of ERK-1 or ERK-2 expression is preferably reduced to substantially normal levels.

As previously described, the method of the present invention inhibits malignant neoplastic growth of epithelial and endothelial cells in a mammal. Malignant cells may exist at the location where they were first transformed, or where they may exist after metastasis.

Malignant neoplastic growth in this specification means any malignant growth of cells (i.e., tumor) that express ERK-1 or ERK-2 in an amount significantly greater that the amount expressed in normal cells of identical origin. The phrase "an amount significantly greater than the amount expressed in normal cells of identical origin" means that the levels of ERK-1 or ERK-2 expression in the malignant growth is at least about 50%, preferably at least about 100%, and more preferably at least about 200% greater than the expression levels of ERK-1 or ERK-2 in normal cells. In fact, expression levels in malignant cells can exceed about 500% and at times can exceed about 1000% and even about 2000% the expression levels of ERK-1 or ERK-2 in normal cells.

Some malignant tumors include, for example, carcinomas, sarcomas, and blastomas. Some examples of cells of epithelial or endothelial origin that can be treated in accordance with the present invention include epithelial and endothelial cells of the breast, prostate, liver, lung and kidney.

The growth of malignant cells is inhibited if the rate of growth is significantly reduced or stopped. The phrase "growth is significantly reduced or stopped" means the growth following treatment in accordance with the invention is at most about 80% of that prior to treatment, preferably at most about 50%, more preferably at most about 30%, and optimally at most about 10%.

The cDNA and amino acid sequences for human ERK-1 and ERK-2 have been described in Charest et al., "Molecular Cloning, Expression, and Characterization of the Human Mitogen-Activated Protein Kinase p44ERK1," *Mol. Cell. Biol.*, Vol. 13, No. 8, 4679–4690 (1993), and in Owaki et al., "Extracellular Signal-Regulated Kinases in T Cells: Characterization of Human ERK-1 and ERK-2 cDNAs," *Biochem. Biophys. Res. Commun.*, Vol. 182, No. 3, 1416–1422 (1992), which are herein incorporated by reference. The sequences for ERK-1 and ERK-2 can also be found in GenBank under Accession Nos. X60188 and M84489, respectively. The sequences disclosed in GenBank are also incorporated herein by reference. However, for the purpose of convenience the cDNA sequences for ERK-1 and ERK-2 are shown below.

The cDNA sequence for human ERK-1 (SEQ ID NO:1) is as follows:

```
cgttcctcgg cgccgccggg gccccagagg gcagcggcag
caacagcagc agcagcagca gcgggagtgg agatggcggc
ggcggcggct caggggggcg ggggcgggga gccccgtaga
accgaggggg tcggcccggg ggtcccgggg gaggtggaga
tggtgaaggg gcagccgttc gacgtgggcc cgcgctacac
gcagttgcag tacatcggcg agggcgcgta cggcatggtc
agctcggcct atgaccacgt gcgcaagact cgcgtggcca
tcaagaagat cagccccttc gaacatcaga cctactgcca
gcgcacgctc cgggagatcc agatcctgct gcgcttccgc
catgagaatg tcatcggcat ccgagacatt ctgcgggcgt
ccaccctgga agccatgaga gatgtctaca ttgtgcagga
cctgatggag actgacctgt acaagttgct gaaaagccag
cagctgagca atgaccatat ctgctacttc ctctaccaga
tcctgcgggg cctcaagtac atccactccg ccaacgtgct
ccaccgagat ctaaagccct ccaacctgct cagcaacacc
acctgcgacc ttaagatttg tgatttcggc ctggcccgga
ttgccgatcc tgagcatgac cacaccggct cctgacgga
gtatgtggct acgcgctggt accgggcccc agagatcatg
ctgaactcca agggctatac caagtccatc gacatctggt
ctgtgggctg cattctggct gagatgctct ctaaccggcc
catcttccct ggcaagcact acctggatca gctcaaccac
attctgggca tcctgggctc cccatcccag gaggacctga
attgtatcat caacatgaag gcccgaaact acctacagtc
tctgcccctcc aagaccaagg tggcttgggc caagcttttc
cccaagtcag actccaaagc ccttgacctg ctggaccgga
tgttaacctt taaccccaat aaacggatca cagtggagga
agcgctggct caccctacc tggagcagta ctatgacccg
acggatgagc cagtggccga ggagcccttc acctcgcca
tggagctgga tgacctacct aaggagcggc tgaaggagct
catcttccag gagacagcac gcttccagcc cggagtgctg
gaggcccct agcccagaca gacatctctg caccctgggg
cctggacctg cctcctgcct gcccctctcc cgccagactg
ttagaaaatg gacactgtgc ccagcccgga ccttggcagc
ccaggccggg gtggagcatg ggcctggcca cctctctcct
ttgctgaggc ctccagcttc aggcaggcca aggccttctc
ctccccaccc gccctcccca cggggcctcg ggagctcagg
tggccccagt tcaatctccc gctgctgctg ctgctgcgcc
cttaccttcc ccagcgtccc agtctctggc agttctggaa
tggaagggtt ctggctgccc caacctgctg aagggcagag
gtggagggtg gggggcgctg agtagggact cagggccatg
cctgccccc tcatctcatt caaaccccac cctagtttcc
ctgaaggaac attccttagt ctcaagggct agcatccctg
aggagccagg ccgggccgaa tcccctcct gtcaaagctg
tcacttcgcg tgccctcgct gcttctgtgt gtggtgagca
gaagtggagc tgggggggcgt ggagagcccg gcgcccctgc
caccctccctg acccgtctaa tatataaata tagagatgtg
tctatggctg aaaaaaaaaa aaaaaa
```

The cDNA sequence for human ERK-2 (SEQ ID NO:2) is as follows:

```
acataatttc tggagccctg taccaacgtg tggccacata
ttctgtcagg aaccctgtgt gatcatggtc tggatctgca
acacgggcca ggccaaagtc acagatcttg agatcacagg
tggtgttgag cagcaggcag gcaggcaatc ggtccgagtg
gctgtcggct cttcagctct ccgctcggcg tcttccttcc
tctcccggtc agcgtcggcg gctgcaccgg cggcgggcag
tcctgcggga ggggcgacaa gagctgaggc gcggccgccg
agcgtcgagc tcagcgcggc ggaggcggcg gcggcccggc
agcaacatg gcggcggcgg cggcggcggg cgcgggcccg
gagatggtcc gcgggcaggt gttcgacgtg gggccgcgct
acaccaacct ctcgtacatc ggcgagggcg cctacggcat
ggtgtgctct gcttatgata atgtcaacaa agttcgagta
gctatcaaga aaatcagccc ctttgagcac cagacctact
gccagagaac cctgagggag ataaaaatct tactgcgctt
cagacatgag aacatcattg gaatcaatga cattattcga
gcaccaacca tcgagcaaat gaaagatgta tatatagtac
aggacctcat ggaaacagat ctttacaagc tcttgaagac
acaacacctc agcaatgacc atatctgcta ttttctctac
cagatcctca gagggttaaa atatatccat tcagctaacg
ttctgcaccg tgacctcaag ccttccaacc tgctgctcaa
caccacctgt gatctcaaga tctgtgactt tggcctggcc
cgtgttgcag atccagacca tgatcacaca gggttcctga
cagaatatgt ggccacacgt tggtacaggg ctccagaaat
tatgttgaat tccaaggct acaccaagtc cattgatatt
tggtctgtag gctgcattct ggcagaaatg ctttccaaca
ggcccatctt tccagggaag cattatcttg accagctgaa
tcacattttg ggtattcttg atccccatc acaagaagac
ctgaattgta taataaattt aaaagctagg aactatttgc
tttctcttcc acacaaaaat aaggtgccat ggaacaggct
```

```
            -continued
gttcccaaat gctgactcca aagctctgga cttattggac aaaatgttga cattcaaccc acacaagagg attgaagtag aacaggctct ggcccaccca tatctggagc agtattacga cccgagtgac gagcccatcg ccgaagcacc attcaagttc gacatggaat tggatgactt gcctaaggaa aagctaaaag aactaatttt tgaagagact gctagattcc agccaggata cagatcttaa atttgtcagg acaagggctc agaggactgg acgtgctcag acatcggtgt tcttcttccc agttcttgac ccctggtcct gtctccagcc cgtcttggct tatccacttt gactcctttg agccgtttgg aggggcggtt tctggtagtt gtggctttta tgctttcaaa gaatttcttc agtccagaga attcactggc c
```

The oligonucleotides of the invention are complementary to at least a portion of the ERK-1 or ERK-2 gene. As used herein, unless otherwise indicated, the term "oligonucleotide" includes both oligomers of ribonucleotides, i.e., oligoribonucleotides, and oligomers of deoxyribonucleotides, i.e., oligodeoxyribonucleotides.

The term "oligonucleotide" includes oligomers and polymers of the biologically significant nucleotides, adenine, deoxyadenine, guanine, deoxyguanine, thymine, uracil, cytosine and deoxycytosine, as well as oligomers and polymers which contain other nucleotides that hybridize to the target mRNA transcript. These terms also include oligomers and polymers having one or more purine or pyrimidine moieties, sugar moieties, or internucleotide linkage(s) that has or have been chemically modified. Such modifications may be substantial and may encompass non-nucleotide chemistries including non-sugar, non-phosphate backbone, and chemical alterations to the bases to maintain the specific hybridization to the mRNA by base-pairing mechanisms, similar to or different from Watson-Crick base pairing. The term "oligonucleotide" further includes those oligomers or polymers that are composed of nucleoside-containing bases joined to the sugar moieties in either the alpha or the beta configuration.

The term "complementary" is used herein to indicate that the oligonucleotide is capable of hybridizing to, and forming a stable duplex with, its targeted sequence of mRNA transcript. The oligonucleotide is also capable of hybridizing with double-stranded DNA to form a triple helix or antigene in which the complementary oligonucleotide binds to dsDNA in the major groove and inhibits transcription.

The length of the antisense oligonucleotide is any length that is complementary to the ERK-1 or ERK-2 mRNA and inhibits its expression. If the oligonucleotide is too short, there may be affinity for sequences other than the targeted nucleic acids. Likewise, if the oligonucleotide is too long, there may be problems of secondary structure, decreased cellular uptake and loss of specificity for ERK-1 and ERK-2. Preferably, the number of nucleotides is not less than about 10, with not less than about 15 nucleotides being more preferred, and not less than about 17 nucleotides being even more preferred. Likewise, the number of nucleotides should preferably not exceed about 100 nucleotides, with not more than about 45 nucleotides being more preferred, and with not more than about 32 nucleotides being even more preferred.

In accordance with the present invention, the oligonucleotide can be complementary to any portion of the mRNA of ERK-1, ERK-2, or both. The complementary portion of the mRNA may include the coding region, the non-coding region, or a combination of both. Preferably, the oligonucleotide, whatever the length may be, includes the methionine initiation codon (ATG) and a sufficient number of nucleotides either upstream and/or downstream of the initiation codon. A particularly suitable oligonucleotide, specific to both ERK-1 and ERK-2, is a 17mer having the sequence 5'-GCC GCC GCC GCC GCC AU-3' (SEQ ID NO:3) or 5'-GCC GCC GCC GCC GCC AT-3' (SEQ ID NO:4), and combinations thereof.

The oligonucleotides of the invention have sufficient complementation to hybridize to contiguous or non-contiguous sequences of the target nucleic acid sequence. "Sufficient complementation" means that at least about 80% of the nucleotides in the oligonucleotide are complementary to, or bind to the target sequence, with about 90% being more preferred, and about 100% being even more preferred.

The oligonucleotides of the invention can be synthesized by any means known in the art. Suitable means include, for example, solid-phase or solution-phase synthesis, preferably in an automated nucleic acid synthesizer or via solution phase techniques. Alternatively, the oligonucleotide may be prepared through the use of reverse transcriptase, PCR synthesis, or via other genetic engineering techniques.

Modifications to the oligonucleotides may be made in order to increase several desirable properties, including solubility, enhanced uptake, or enhanced stability to degradation, for example. Thus, modifications to the phosphate backbone, termini, sugar moiety, or the individual nucleic acid bases are within the scope of this invention. For example, the phosphodiester linkage between the sugar moieties may be modified. A suitable modification involves the use of phosphorothioate linkages between the sugar moieties. The combination of various modifications, for example, phosphate backbone modifications in combination with any number of terminal conjugates, is also within the scope of this invention. The terminal modifications may include cross-linking agents, intercalators, photochemically activated moieties, alkylating agents and redox active nucleic acid cleavage groups.

The oligonucleotide of the present invention may be administered by any means that causes transmission into malignant cells. The oligonucleotide may be administered to the mammal locally or systemically.

The local administration of the oligonucleotide can be accomplished by inserting the oligonucleotide directly into the malignant neoplastic growth, or into the tissue surrounding the growth and permitting the oligonucleotide to migrate to, and enter the malignant cells. For example, tumors that are accessible to a syringe needle, such as breast tumors, can be treated by injecting the oligonucleotides into the tumor and/or into the tissue surrounding the tumor. The injection may be intramuscular, intravenous, intraperitoneal, or subcutaneous. The oligonucleotide may be administered to the liver through the hepatic portal system. Similarly, the oligonucleotide can be administered to the lung by use of a pulmonary inhaler.

However, other modes of administering the oligonucleotides systemically or topically can also be utilized. For example, the oligonucleotides can be administered systemically in an expression vector. The term "expression vector" refers to a plasmid, virus or other vehicle known in the art that has been manipulated by insertion or incorporation of an antisense oligonucleotide. Vectors suitable for use in the present invention include, the pMSXND expression vector (Lee and Nathans, *J. Biol. Chem.*, Vol. 263, 3521 (1988))

and eukaryotic viral vectors, such as simian virus 40 (SV40), bovine papilloma virus (Eukaryotic Viral Vectors, Cold Spring Harbor Laboratory, Gluzman ed., (1982)), adenovirus, and adeno-associated virus. Examples of adeno-associated virus vector, and methods of their preparation, can be found in U.S. Pat. Nos. 5,173,414 and 5,354,678. A particularly preferred vector system to be utilized is an expression vector incorporating the phosphoenolpyruvate carboxykinase (PEPCK) gene as described in Moxham et al., "Induction of $G_{\alpha 12}$-Specific Antisense RNA in Vivo Inhibits Neonatal Growth," *Science,* Vol. 260, 991–995 (1993), which is herein incorporated by reference.

Preferably, the expression vector will contain a promoter that will allow for efficient production of the antisense oligonucleotide in the mammal, and preferably constitutive production of the oligonucleotide. For example, the promoter can be a polyhedrin promoter.

The expression vector will also preferably be targeted for expression of the oligonucleotide at the site of the malignant neoplasm. This can be accomplished by placing the oligonucleotide under the control of a promotor specific for the targeted cell, e.g., epithelial or endothelial. An example of such a promotor is a mammary tumor virus promoter, such as the murine mammary tumor virus (MuMTV) promoter, which is especially useful for treatment of breast cancers. Other examples of promoters specific for breast tissue are promoters for milk proteins, such as whey acidic protein, β-lactoglobulin, $\alpha_{s1}$-casein, and β-casein. Promoters for milk proteins are particularly suitable since expression may be induced with lactogenic agents.

As previously described, the oligonucleotide of the present invention is administered to a mammal. Since ERK-1 and ERK-2 are highly conserved among mammals, the present invention is readily adapted to all mammalian species. Some examples of mammals include domesticated animals, simians and humans. Domesticated animals include those of the following species: canine; feline; bovine; equine; porcine; and murine.

The present invention also includes a dosage unit containing an effective amount of an oligonucleotide complementary to at least a portion of the mRNA of ERK-1 or ERK-2 for the mammal to be treated. The amount contained in the dosage unit is effective to decrease expression of the MAP kinase.

In accordance with the present invention, the dosage unit can be in any form. As will be apparent to the skilled artisan, the concentration of the oligonucleotide will vary with the choice of administration to the mammal. For example, if the oligonucleotide is administered by injection to the mammal, the dosage unit is a syringe containing an effective amount of the oligonucleotide. An effective amount of the oligonucleotide for systemic administration can range from about 0.01 mg/Kg to 50 mg/Kg administered once or twice per day. However, different dosing schedules can be utilized depending on (i) the potency of an individual oligonucleotide at inhibiting expression, (ii) the severity or extent of the pathological disease state, or (iii) the pharmacokinetic behavior of a given oligonucleotide.

The oligonucleotide can be combined with a pharmaceutically acceptable carrier or an excipient. Some examples of excipients include fillers, extenders, binders, disintegrants, surface-active agents or lubricants depending on the nature of the administration and dosage forms. Typical dosage forms include tablets, powders, liquid preparations, including suspensions, emulsions and solutions, granules, capsules, suppositories as well as liquid preparations for injections including liposome preparations.

For administration in mammals, the oligonucleotides of the invention are advantageously formulated in liquid solutions, preferably in physiologically compatible buffers such as Hank's solution or Ringer's solution. In addition, the oligonucleotides can be formulated in solid form and redissolved or suspended immediately prior to use. Lyophilized forms and liposomes containing oligonucleotides are also included.

For topical administration, the oligonucleotides of the invention may be formulated in liquid solutions, as described above, or in ointments, salves, gels, or creams, as is generally known in the art. Formulation of the invention oligomers for ocular indications is based on standard compositions known in the art.

The oligonucleotides of the invention may also be administered by any method known in the art for systemic administration. Some suitable methods for systemic administration include, for example, transmucosal, transdermal, or oral methods. For transmucosal or transdermal administration, penetrants appropriate to the barrier to be permeated may be used in the formulation. Such penetrants are generally known in the art, and include, for example, bile salts and fusidic acid derivatives for transmucosal administration. In addition, enhancers can be used to facilitate permeation. Transmucosal administration can be through use of nasal sprays, for example, or suppositories. For oral administration, the oligonucleotides are formulated into conventional oral administration forms such as capsules, tablets, and tonics.

The present invention also includes a method of identifying and monitoring potentially malignant neoplastic cell growth in a mammal. Cells from a tissue sample that are malignant or potentially malignant are obtained from the mammal. Thereafter, the mRNA that encodes ERK-1 or ERK-2, or the ERK-1 or ERK-2 protein, may be isolated for assay, or may be assayed in situ.

The first step of the assay is to determine the level of expression of ERK-1 or ERK-2 in the epithelial or endothelial cells obtained from the mammal being tested for malignant neoplastic growth. The second step is to ascertain whether the level of expression determined in the first step is higher than a baseline level of expression of the same MAP kinase found, or expected, in normal cells of similar, preferably identical, origin. The phrase "higher level" means that the level of expression is at least about 50% greater than in normal cells, with at least about 100% being more preferred, and with at least about 200% being even more preferred. However, as previously described, expression levels exceeding 500%, 1000%, and even 2000%, may be observed.

The term "expression" is meant to include the transcription of DNA to produce mRNA that encodes either ERK-1 or ERK-2, and the translation of the mRNA to produce MAP kinases.

The ability to compare the two levels of expression allows for an effective method of identifying potentially malignant neoplastic cell growth and for monitoring such cell growth after being identified as malignant. A higher level of expression of at least about 50%, more preferably at least about 100%, and even more preferably at least about 200%, is used for determination of malignancy.

As a result of this ability to quantify cellular alterations for discerning malignancies, pathologists do not have to solely rely on phenotypical alterations to make a diagnosis. This is especially important in monitoring potentially malignant conditions such as proliferative breast disease. Proliferative breast disease involves a spectrum of phenotypical alterations in which a pathologist must discern, e.g., adenosis, sclerosis, hyperplasia (ductal, lobular and apocrine) with or without atypia, noninvasive carcinoma and invasive carcinoma. A pathologist's diagnosis between these stages, e.g., hyperplasia and carcinoma, is dependent on his or her abillity to discern such subtle changes in phenotype. The experience of the pathologist will often be a deciding factor in discerning such changes, which can lead to varying diagnosis among pathologists. Thus, a quantifiable method of identifying and monitoring potentially malignant neoplastic cell growths provides pathologists with a uniform method to assist them in diagnosis.

The sample of the neoplastic cell growth can be removed from the mammal following standard biopsy techniques. Preferably, the samples of the neoplastic cell growth can be remove by needle biopsy and subjected immediately to analysis of expression of ERK-1 and ERK-2. A significant advantage of the invention is that a determination of malignancy can be made within a few hours, as compared to a few days following conventional histopathology. Thus, the invention dramatically shortens the time generally needed for a determination of malignancy following a biopsy.

If desired, the tissue sample can also be excised from the mammal and processed for later analysis in accordance with the invention. For example, the tissue sample may be sectioned, frozen and stored in liquid nitrogen or helium. In any event, it is preferable not to culture the cells prior to conducting the assay.

The baseline level of expression is determined from a tissue sample of normal cells of similar, preferably identical, origin. The tissue sample of normal cells is obtained from the same mammal or from another mammal having a similar, preferably identical background. For example, with the advent of core biopsy techniques, in which a core sample of the tumor and surrounding normal tissue is taken, tissue samples for a determination of malignancy need only be taken once from the mammal.

The baseline level of expression need not be determined at the same time as the level of expression from the test sample. A baseline level of expression can be determined for various cell types from various mammals, especially from humans, and used in later assays.

The level of ERK-1 or ERK-2 mRNA can be determined by standard methods known in the art. Such methods generally involve the use of a labeled probe. The probe may be an antibody that recognizes the ERK-1 or ERK-2 protein, or a fragment thereof, or an oligonucleotide that recognizes RNA or DNA encoding the ERK-1 or ERK-2 protein.

For example, the level of mRNA may be determined by northern blotting with the appropriate labeled nucleic acid probes. The probes may be RNA or DNA molecules, such as the oligonucleotides of the invention described above for use as antisense oligonucleotides. The labeled probes are quantitated by standard methods known in the art.

The length of the oligonucleotide probe is not critical, as long as it is capable of hybridizing to the target nucleic acid. The oligonucleotide probe should contain at least about 6 nucleotides, preferably at least about 10 nucleotides, and, more preferably, at least about 15 nucleotides.

There is no upper limit to the length of the oligonucleotide probes. Longer probes are more difficult to prepare and require longer hybridization times. Therefore, the probe should not be longer than necessary. Normally, the oligonucleotide probe will not contain more than about 50 nucleotides, preferably not more than about 40 nucleotides, and, more preferably, not more than about 30 nucleotides.

The probes described above are labeled in accordance with methods known in the art. The label may be a radio-active atom, an enzyme, or a chromophoric moiety. Methods for labeling oligonucleotide probes have been described, for example, by Leary et al., *Proc. Natl. Acad. Sci.* USA, Vol. 80, 4045 (1983); Renz and Kurz, *Nucl. Acids Res.,* Vol. 12, 3435 (1984); Richardson and Gumport, *Nucl. Acids Res.,* Vol. 11, 6167 (1983); Smith et al., *Nucl. Acids Res.,* Vol. 13, 2399 (1985); and Meinkoth and Wahl, *Anal. Biochem.,* Vol. 138, 267 (1984).

Alternatively, the level of mRNA expression may be determined with reverse transcriptase polymerase chain reaction (RT-PCR) as described in G. J. Nuovo., in situ *Hybridization: Protocols and Applications,* 2nd edition, Raven Press, New York 1994, incorporated herein by reference. The level of mRNA expression can be determined in vivo or in vitro.

The level of ERK-1 or ERK-2 proteins may also be determined by standard techniques known in the art. Typically, an immunoassay, such as western blotting or ELISA, is performed (Sale et al., "Requirement of MAP Kinase for Differentiation of Fibroblasts to Adipocytes, for Insulin Activation of p90 S6 Kinase and for Insulin or Serum Stimulation of DNA Synthesis," *EMBO J.,* Vol. 14, No. 4, 674–684 (1995); Gao, Ping and Malbon, Craig C., "Morphogen-induced Decline in $G_{i\alpha2}$ Triggers F9 Teratocarcinoma Stem Cell Progression via Phospholipase C and Mitogen-activated Protein Kinase,"*J. Biol. Chem.,* Vol. 271, No. 15, 9002–9008 (1996); Boulton, T. G. and Cobb, M. H., "Identification of Multiple Extracellular Signal-regulated Kinases (ERKs) with Antipeptide Antibodies," *Cell Reg.,* Vol. 2, 357–371 (1991)). Alternatively, the level of ERK-1 or ERK-2 expression may be determined by other standard techniques, such as by immunohistochemical staining and immunoprecipitation.

The immunoassays for detecting the presence of proteins with antibodies are normally based on incubating an antibody with a sample suspected of containing the protein and detecting the presence of a complex between the antibody and the protein. The antibody is labeled either before, during, or after the incubation step. The protein is preferably immobilized prior to detection. Immobilization may be accomplished by directly binding the protein to a solid surface, such as a microtiter well, or by binding the protein to immobilized antibodies.

In a preferred embodiment, a protein is immobilized on a solid support through an immobilized first antibody specific for the protein. The immobilized first antibody is incubated with a sample suspected of containing the protein. If present, the protein binds to the first antibody.

A second antibody, also specific for the protein, binds to the immobilized protein. The second antibody may be labeled by methods known in the art. Non-immobilized materials are washed away, and the presence of immobilized label indicates the presence of the protein. This and other immunoassays are described by David et al., in U.S. Pat. No. 4,376,110 assigned to Hybritech, Inc., LaJolla, Calif.

Immunoassays may involve one step or two steps. In a one-step assay, the target molecule, if it is present, is immobilized and incubated with a labeled antibody. The labeled antibody binds to the immobilized target molecule. After washing to remove unbound molecules, the sample is assayed for the presence of the label.

In a two-step assay, immobilized target molecule is incubated with an unlabeled first antibody. The target molecule-antibody complex, if present, is then bound to a second, labeled antibody that is specific for the unlabeled antibody. The sample is washed and assayed for the presence of the label, as described above.

The immunometric assays described above include simultaneous sandwich, forward sandwich, and reverse sandwich immunoassays. These terms are well known to those skilled in the art.

In a forward sandwich immunoassay, a sample is first incubated with a solid phase immunoabsorbent containing antibody against the protein. Incubation is continued for a period of time sufficient to allow the protein in the sample to bind to the immobilized antibody in the solid phase. After the first incubation, the solid phase immunoabsorbent is separated from the incubation mixture and washed to remove excess protein and other interfering substances which also may be present in the sample. Solid phase immunoabsorbent-containing protein bound to the immobilized antibodies is subsequently incubated for a second time with soluble labeled antibody cross-reactive with a different domain on the protein. After the second incubation, another wash is performed to remove the unbound labeled antibody from the solid immunoabsorbent and to remove non-specifically bound labeled antibody. Labeled antibody bound to the solid phase immunoabsorbent is then detected and the amount of labeled antibody detected serves as a direct measure of the amount of antigen present in the original sample. Alternatively, labeled antibody that is not associated with the immunoabsorbent complex can also be detected, in which case the measure is in inverse proportion to the amount of antigen present in the sample. Forward sandwich assays are described, for example, in U.S. Pat. Nos. 3,867,517, 4,012,294; and 4,376,110.

In a reverse sandwich assay, the sample is initially incubated with labeled antibody. The solid phase immunoabsorbent containing immobilized antibody cross-reactive with a different domain on the protein is added the labeled antibody, and a second incubation is carried out. The initial washing step required by a forward sandwich assay is not required, although a wash is performed after the second incubation. Reverse sandwich assays have been described, for example, in U.S. Pat. Nos. 4,098,876 and 4,376,110.

In a simultaneous sandwich assay, the sample, the immunoabsorbent with immobilized antibody, and labeled soluble antibody specific to a different domain are incubated simultaneously in one incubation step. The simultaneous assay requires only a single incubation and does not require any washing steps. The simultaneous assay is a very useful technique, providing ease of handling, homogeneity, reproducibility, linearity of the assays, and high precision. See U.S. Pat. No. 4,376,110 to David et al.

In each of the above assays, the sample containing the ERK 1- and/or ERK-2 proteins, the solid phase immunoabsorbent with immobilized antibody, and the labeled soluble antibody are incubated under conditions and for a period of time sufficient to allow the proteins to bind to the immobilized antibodies and to the soluble antibodies. In general, it is desirable to provide incubation conditions sufficient to bind as much protein as possible, since this maximizes the binding of labeled antibody to the solid phase, thereby increasing the signal. The specific concentrations of labeled and immobilized antibodies, the temperature and time of incubation, as well as other such assay conditions, can be varied, depending upon various factors including the concentration of protein in the sample, the nature of the sample an the like. Those skilled in the art will be able to determine operative and optimal assay conditions for each determination by employing routine experimentation.

There are many solid phase immunoabsorbents which have been employed and which can be used in the present invention. Well known immunoabsorbents include beads formed from glass, polystyrene, polypropylene, dextran, nylon, and other material; and tubes formed from or coated with such materials, and the like. The immobilized antibodies may be covalently or physically bound to the solid phase immunoabsorbent, by techniques such as covalent bonding via an amide or ester linkage or by absorption.

Methods for labeling antibodies suitable for immunoassays have been described, for example, by Hunter and Greenwood, *Nature,* Vol. 144, 945 (1962) and by David et al., *Biochemistry,* Vol. 13, 1014–1021 (1974). Additional methods for labeling antibodies have been described in U.S. Pat. Nos. 3,940,475 and 3,645,090.

The label for the oligonucleotide, antibody or fragment thereof may be radioactive. Some examples of useful radioactive labels include $^{32}P$, $^{125}I$, $^{131}I$, and $^{3}H$. Use of radioactive labels have been described in U.K. 2,034,323, U.S. Pat. No. 4,358,535, and U.S. 4,302,204.

Some examples of non-radioactive labels include enzymes, chromophors, atoms and molecules detectable by electron microscopy, and metal ions detectable by their magnetic properties.

Some useful enzymatic labels include enzymes that cause a detectable change in a substrate. Some useful enzymes and their substrates include, for example, horseradish peroxidase (pyrogallol and o-phenylenediamine), beta-galactosidase (fluorescein beta-D-galactopyranoside), and alkaline phosphatase (5-bromo-4-chloro-3-indolyl phosphate/nitro blue tetrazolium). The use of enzymatic labels have been described in U.K. 2,019,404, EP 63,879, and by Rotman, *Proc. Natl. Acad. Sci.,* Vol. 47, 1981–1991 (1961).

Useful chromophores include, for example, fluorescent, chemiluminescent, and bioluminescent molecules, as well as dyes. Some specific chromophores useful in the present invention include, for example, fluorescein, rhodamine, Texas red, phycoerythrin, umbelliferone, luminol.

The labels may be conjugated to the antibody or nucleotide probe by methods that are well known in the art. The labels may be directly attached through a functional group on the probe. The probe either contains or can be caused to contain such a functional group. Some examples of suitable functional groups include, for example, amino, carboxyl, sulfhydryl, maleimide, isocyanate, isothiocyanate.

Alternatively, labels such as enzymes and chromophoric molecules may be conjugated to the antibodies or nucleotides by means of coupling agents, such as dialdehydes, carbodiimides, dimaleimides, and the like.

The label may also be conjugated to the oligonucleotide or antibody by means of a ligand attached to the probe by a method described above and a receptor for that ligand attached to the label. Any of the known ligand-receptor combinations is suitable. Some suitable ligand-receptor pairs include, for example, biotin-avadin or -streptavadin, and antibody-antigen. The biotin-avidin combination is preferred.

The antibodies used in the assays described above may be polyclonal or monoclonal. Polyclonal antibodies may be isolated from mammals that have been innoculated with the ERK-1 or ERK-2 protein or a functional analog in accordance with methods known in the art. Briefly, polyclonal antibodies may be produced by injecting a host mammal, such as a rabbit, mouse, rat, or goat, with the protein or a fragment thereof capable of producing antibodies that is specific for ERK-1 or ERK-2. Serum from the mammal is extracted and screened to obtain polyclonal antibodies that are specific to ERK-1 or ERK-2.

The antibodies are preferably monoclonal. Monoclonal antibodies may be produced by methods known in the art.

These methods include the immunological method described by Kohler and Milstein, *Nature,* Vol. 256, 495–497 (1975) and by Campbell, "Monoclonal Antibody Technology, The Production and Characterization of Rodent and Human Hybridomas", in Burdon et al., Eds, Laboratory Techniques in Biochemistry and Molecular Biology, Vol. 13, Elsevier Science Publishers, Amsterdam 1985; as well as the recombinant DNA method described by Huse et al., *Science,* Vol. 246, 1275–1281 (1989).

As will be demonstrated in the following non-limiting examples, the methods of the present invention are especially applicable to identifying, monitoring and treating breast cancer in a mammal.

EXAMPLES

Unless indicated otherwise, gel electrophoresis, immunoblotting, immunostaining, and immunoprecipitation are standard techniques, as described in Sambrook et al., *Molecular Cloning: A Laboratory Manual,* Vol. 1–3, 2nd edition, Cold Spring Harbour Laboratory Press, New York 1989.

Example 1

Increased levels of MAP Kinase Activity in Primary Breast Carcinoma Samples A total of 37 breast tissue samples were taken from the following patients: five with normal breast tissue, one with gynecomastia, four with benign fibroadenoma, five with fibrocystic disease, one with fibrocystic disease and fibroadenoma, two with chronic inflammatory disease, eleven who were subsequently identified as having primary breast carcinoma, and one with carcinosarcoma.

The excised tissue samples were sectioned, frozen, stored temporarily at −80° C., and placed in liquid nitrogen for storage. Frozen samples were then removed from storage, placed in liquid nitrogen and mechanically pulverized. The resultant powder was reconstituted into a lysis buffer (70 mM β-glycerophosphate (pH 7.2), 0.1 mM sodium vanadate, 2 mM $MgCl_2$, 1 mM EGTA, 1 mM dithiothreitol, 0.5% (v/v) Triton X-100, 0.2 mM phenylmethylsulfonyl fluoride, 5 mg/ml Leupeptin, 2 mg/ml aprotinin).

MAP kinase activity was measured using EGF receptor peptide as the substrate as described in Gupta et al., "MAP kinase is constitutively active in gip2 and src transformed rat HeLa cells," *J. Biol. Chem.,* Vol. 267, 7987–7990 (1992). The MAP kinase activity of each sample was analyzed in triplicate, and on more than one occassion. The representative results of tissue samples taken from ten of the patients are shown in FIG. 1, which are grouped as four different pathology states.

Figure 1:
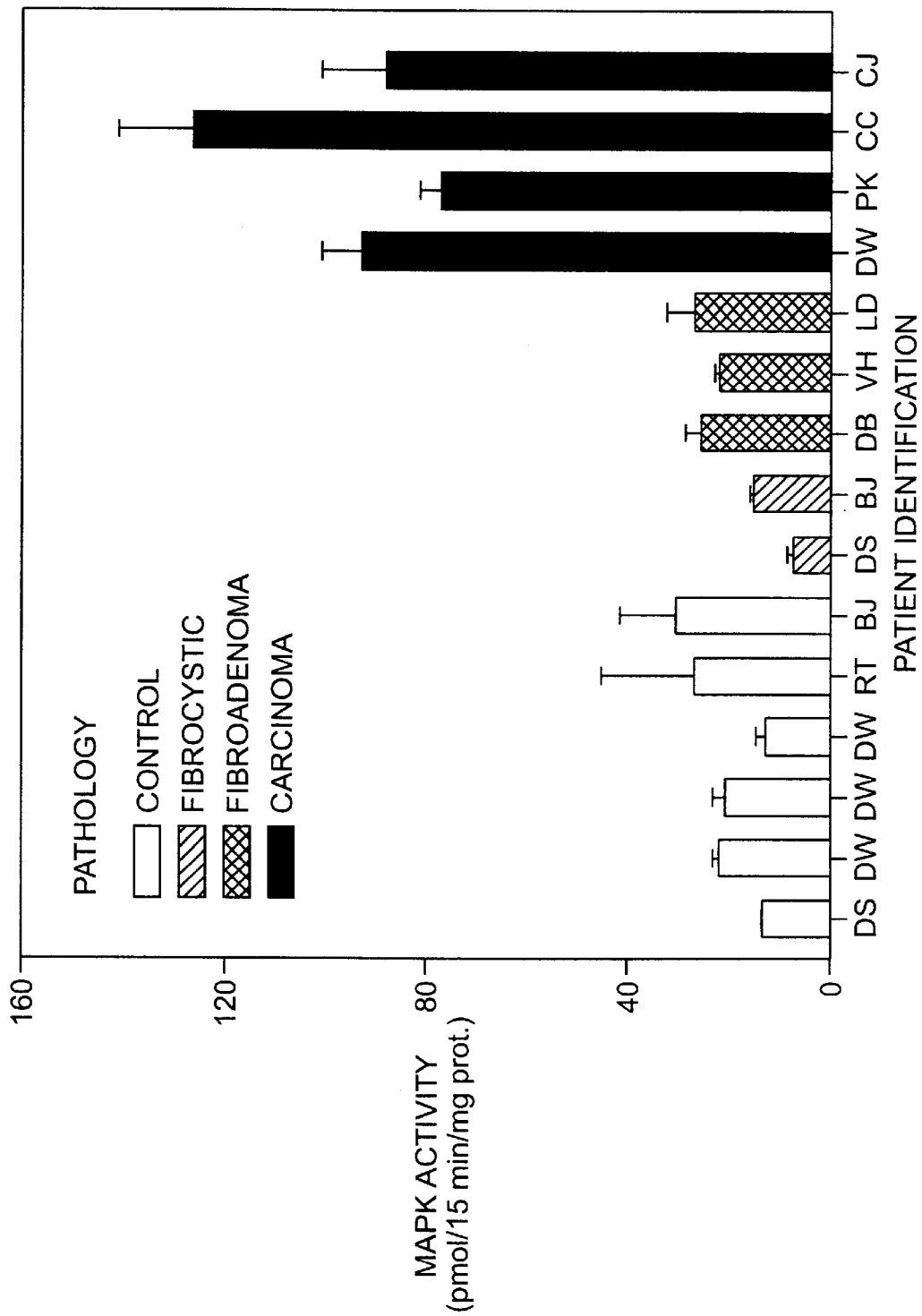
FIG. 1 is a bar graph of MAP kinase activity of extract taken from breast tissue samples of patients with carcinoma, benign fibroadenoma, fibrocystic disease and normal tissue.

As can be seen in FIG. 1, the primary breast carcinoma samples exhibited increased levels of MAP kinase activity. For example, in one patient, MAP kinase activity was 4–5-fold higher in the malignant tissue sample analyzed than any of the three normal (non-malignant) tissue samples that were analyzed.

These findings were consistent in all eleven patients with breast cancer, who all exhibited markedly elevated MAP kinase activity. MAP kinase activity (pmol/min/mg protein) was 1.40±0.19 (mean±S.E.M., n=6) for tissue from the control study group as compared to 6.39±0.71 (p≦0.05 for the difference) for the tissue from patients with primary breast carcinoma.

Example 2

The Over Expression of MAP Kinase is One of the Causes for MAP Kinase Over Activation in Breast Cancer In order to determine the cause for the increased activation of MAP kinase in primary breast carcinoma, MAP kinase expression was determined in some of the breast tissue samples described in Example 1. Specifically, breast tissue samples from patients with fibrocystic disease (FC), benign fibroadenoma (FA) and carcinoma of the breast (CA) were utilized.

The tissue samples were processed according to the procedure described in Example 1. Samples of tissue extract (i.e., cellular proteins) were subjected to SDS-PAGE on 10% acrylamide separating gels at 50 μg/lane. The separated proteins were transferred to nitrocellulose blots and immunecomplexed with a primary antibody specific for human MAP kinase (BRL Laboratories, Gaithersberg, Md.), and made visible by alkaline phosphatase-conjugated second antibody staining of the immunecomplexes, following the procedure in Moxham et al., "Mammalian beta 1- and beta2-adrenergic receptors, immunological and structural comparisons," *J. Biol. Chem.,* Vol. 261, 14562–14570 (1986). More specifically, the blots were prepared, stained with primary antibodies, washed, stained with the second antibody and then incubated at 22° C. with substrate solution (5.0 ml of 50 mM glycine (pH 9.6), 0.17 mg/ml p-nitro blue tetrazolium chloride, 7 mM $MgCl_2$, and 0.08 mg/ml 5-bromo-4-chloro-3-indoyl phosphate) until bands were visible (approximately 30 sec). The reaction was terminated by washing free the substrate solution and rinsing with distilled water. The stained immunoblot is shown in FIG. 2.

Figure 2:
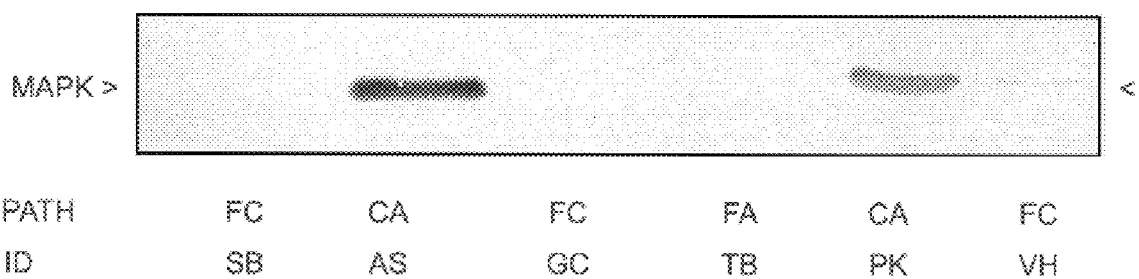
FIG. 2 is a photograph of a nitrocellulose blot of MAP kinase isolated from extracts of breast tissue taken from patients with carcinoma (CA), benign fibroadenoma (FA), and fibrocystic disease (FC).

From FIG. 2, marked overexpression of MAP kinase in breast cancer is evidenced by the highly visible band. However, with the tissue samples of benign fibroadenoma and fibrocystic disease, there was little if any staining of MAP kinase under the same conditions. Thus, this example demonstrates that the overexpression of MAP kinase is one of the causes for MAP kinase overactivation in breast cancer.

Example 3

The Increased Levels of MAP Kinase Activation are Due to Over Expression

Because breast tissue is heterogeneous with respect to cell-type, the identity of cell-types responsible for the elevated expression of MAP kinase was investigated. Thin sections approximately 4 microns thick were sliced from paraffin blocks of primary breast carcinoma tissue. The sections were all stained eosin and hematoxylin following conventional histopathology. One representative stained section is shown in panel A of FIG. 3. The cancer cells are highlighted by arrows.

The remaining sections were then subjected to in situ RT-PCR following the procedure described in Nuovo et al., "Correlation of the in situ detection of polymerase chain reaction-amplified metalloproteinase complementary DNAs and their inhibitors with prognosis in cervical carcinoma," *Cancer Res.,* Vol. 55, 267–275 (1995), and in G. J. Nuovo, in situ *Hybridization. Protocols and Applications,* 2nd edition, Raven Press, New York 1994. Digoxigenin (in the form of dUTP) was employed as the reporter molecule for PCR. An anti-digoxigenin antibody coupled to alkaline phosphatase employed with a chromogen was utilized to make visible (blue staining) the PCR products.

Controls for the RT-PCR experiment were prepared in the following manner. A negative control was prepared using PCR primers for an unrelated hepatitis C viral RNA (sense orientation, TCCGCGGCCGCACTCCACCATGAAT-CACTCCCC (SEQ ID NO:5); antisense orientation, AGTCTTGCGGCCGCAGCGCCAAATC (SEQ ID NO:6)) after DNAse digestion. The negative control is shown in panel B of FIG. 3. A positive control was prepared using PCR primers for MAP kinase (sense orientation, GCAG-GTGTTCGACGTGGG (SEQ ID NO:7); antisense orientation, GTGCAGAACGTTAGCTGAAT (SEQ ID NO:8)) and genomic DNA in the absence of pretreatment with DNAse. The positive control is shown in panel C of FIG. 3. High levels of MAP kinase mRNA expression can be seen as intense blue staining.

The test sections were analyzed using PCR primers for MAP kinase after treatment with DNAse, followed by RT-PCR. The analyzed sections are shown in panels D, E, and F of FIG. 3. In order to provide a comparison between benign and malignant tissue samples from a single patient, samples from patient DW were analyzed by in situ RT-PCR of MAP kinase mRNA. These results are shown in panel E (benign sample) and panel F (malignant sample).

From the analyzed sections, it was surprisingly found that the MAP kinase mRNA was highly expressed only in the epithelial cells of the primary breast carcinoma samples. Digestion with DNAase followed by in situ RT-PCR provided the first evidence (intense blue staining) for high levels of MAP kinase mRNA in the cytoplasm of cancerous epithelial cells (shown by arrows). However, as can be seen in panels D and F, the surrounding stromal and adipose cells did not exhibit intense staining. Likewise, benign fibroadenomatous tissue only exhibited an occasional weak signal in the epithelial cells (data not shown). Thus, the discovery of in vivo MAP kinase overexpression in cancer cells of epithelial origin provides a unique opportunity for diagnosis and treatment.

Example 4

Over Expression of MAP Kinase Occurs in Metastatic Sites

In situ RT-PCR was performed on lymph node tissue having metastasized primary breast carcinoma to investigate MAP kinase overexpression in metastatic cancer. Thin sections approximately 4 microns thick were sliced from paraffin blocks of lymph node tissue having metastasized primary breast carcinoma tissue. The sections were analyzed following the procedure set forth in Example 3.

The results of the lymph node sections analyzed are shown in FIG. 4, which can be described in the following manner. Panel A of FIG. 4 shows the section analyzed with eosin and hematoxylin staining, which reveals metastatic cancer cells in the lymph node as indicated by arrows. Panel B of FIG. 4 shows the section acting as a negative control, which exhibits no blue staining. Panel C shows the section acting as a positive control exhibiting intense nuclear blue staining in all cancer cells. Panel D shows the test section which exhibits intense nuclear blue staining in all cancer cells, but virtually no staining in the surrounding stromal cells. These results demonstrate that the overexpression MAP kinase is also localized in the metastatic sites of epithelial cancers.

Example 5

Confirmation of In Vivo Over Expression of MAP Kinase

Sections of primary breast carcinoma and metastasized lymph node tissue were subjected to immunohistochemical analysis to confirm the expression of MAP kinase in vivo. Following conventional histopathology, the sections were all stained with eosin and hematoxylin. The sections were then analyzed as described in Nuovo et al., "In situ detection of PCR-amplified HIV-1 nucleic acids and tumor necrosis factor cDNA in cervical tissues," *Amer. J. Pathol.*, Vol. 143, 40–48 (1993), utilizing a murine monoclonal antibody to human MAP kinase (Zymed, South San Francisco, Calif.), which were made visible by use of a second, biotinylated antibody, followed by alkaline phosphatase-conjugated streptavadin and a fast red substrate.

From panels A and B of FIG. 5, the overexpression of MAP kinase is clearly seen in the analyzed sections of primary and metastatic breast cancer, respectively. Intense red staining was observed in the cytoplasm of cancerous epithelial cells (indicated with arrows) at both the primary and metastatic sites.

Example 6

Patients With Primary Breast Carcinoma Exhibit Increased Levels of Fully Active MAP Kinase Tissue samples were excised, sectioned, frozen and had extracts prepared as described Example 2. The samples of cellular protein then were further processed in one of three manners described below.

One set of tissue extract samples was directly subjected to SDS-PAGE and immunoblot staining following the procedure of Example 2, with two modifications. First, the murine monoclonal antibody of Example 5 was used as the primary antibody. Second, protein markers were utilized to determine the mobility of MAP kinase. The results of the immunoblot staining for three of the pathology states (normal (C), fibrocystic disease (FC), and carcinoma (CA)) are shown in panel A of FIG. 6.

A second set of tissue extract samples was subjected to immunoprecipitation, SDS-PAGE and immunoblot staining, in the following manner. Sampling tissue extract (approximately 0.6 mg protein) was immunoprecipitated using either the murine monoclonal antibody of Example 5 or a rabbit polyclonal antibody (ProMega, Madison, Wis.) which is specific for the dually phosphorylated (serine and tyrosine) "active" form of MAP kinase. The results of the immunoblot staining are shown in panel C of FIG. 6. The immunoprecipitate was then subjected to SDS-PAGE and immunoblot staining as previously described in this example, but with an anti-phosphotyrosine antibody (Transduction Laboratories, Lexington, Ky.) as the primary antibody. The results of the immunoblot staining are shown in panel B of FIG. 6.

A third set of tissue extract samples was directly subjected to SDS-PAGE and immunoblot staining as previously described in this example, but with the previously described rabbit polyclonal antibody as the primary antibody. The results of the immunoblot staining are shown in panel C of FIG. 6.

The results of the immunoblots can be summarized in the following manner. Panel A demonstrates that while there was some limited MAP kinase expression in non-malignant tissue, primary breast carcinoma still exhibited significantly higher levels of MAP kinase. Panel B demonstrates that patients with primary breast carcinoma also exhibit increased levels of MAP kinase phosphorylated at the tyrosine residue. Likewise, panel C demonstrates that patients with primary breast carcinoma exhibit increased levels of MAP kinase that is dually phosphorylated, i.e., fully active. Thus, patients with primary breast carcinoma not only exhibit increased levels MAP kinase expression but exhibit increased levels of fully active MAP kinase.

Example 7

Confirmation that Primary Breast Carcinomas Exhibit Fully Active MAP Kinase

In order to confirm the finding of MAP kinase overactivation found in Example 6, additional immunoblot analysis was conducted. Samples of tissue extracts from a patient (VH) with fibrocystic disease (FC) and a patient (PK) with primary breast carcinoma (CA) were prepared for SDS-PAGE and immunoblot staining following the procedure of Example 2, but with the following modification. The immunoblots were stained with the previously described antibodies against either MAP kinase (MAPK) or phosphotyrosine (PY). The results of the immunoblot staining are shown in FIG. 7.

From FIG. 7, it is readily apparent that phosphorylation on tyrosyl residues is elevated in MAP kinase overexpressed in primary breast carcinoma. Equal amounts of protein loading (50 µg/lane) of samples taken from both patients confirm that not only is the amount of MAP kinase increased, but also its phosphorylation state is increased in primary breast cancer.

We claim:

1. A method of inhibiting growth of malignant lung tumors in a mammal, which comprises injecting directly into the tumor or administering to the lung of said mammal in an aerosolized form an effective amount of an oligonucleotide having 10–100 nucleotides and complementary to the initiation region of ERK-1 or ERK-2.

2. The method of claim 1, wherein said oligonucleotide has about 15 to about 45 nucleotides.

3. The method of claim 2, wherein said oligonucleotide has about 17 to about 32 nucleotides.

4. The method of claim 3, wherein said oligonucleotide is an oligonutcleotide selected from the group consisting of SEQ ID NO:3, SEQ ID NO:4 and mixtures thereof.

5. The method of claim 1, wherein said oligonucleotide is in an expression vector.

6. A method according to claim 1 wherein said administration to the lung in an aerosolized form is by a pulmonary inhaler.

* * * * *

UNITED STATES PATENT AND TRADEMARK OFFICE
CERTIFICATE OF CORRECTION

PATENT NO.     : 6,271,210 B1
DATED          : August 7, 2001
INVENTOR(S)    : Sivaraman et al.

It is certified that error appears in the above-identified patent and that said Letters Patent is hereby corrected as shown below:

<u>Column 3,</u>
Line 50, now reads "As a result of the se" should read -- As a result of these --;
Line 54, now reads "cultured cell fines" should read -- cultured cell lines --;

<u>Column 4,</u>
Line 61, now reads -- BRIEF DESCRIPTION OF TIE DRAWINGS" should read
-- BRIEF DESCRIPTION OF THE DRAWINGS --;

<u>Column 16,</u>
Line 15, now reads "include $^{32}$p, $^{125}$I, $^{131}$I and $^{3}$H" should read -- include $^{32}$P, $^{125}$I, $^{131}$I and $^{3}$H --.

Signed and Sealed this

Sixteenth Day of April, 2002

Attest:

JAMES E. ROGAN
*Attesting Officer*    *Director of the United States Patent and Trademark Office*

SEQUENCE LISTING

```
<160> NUMBER OF SEQ ID NOS: 4

<210> SEQ ID NO 1
<211> LENGTH: 1866
<212> TYPE: DNA
<213> ORGANISM: Homo sapiens
<220> FEATURE:
<223> OTHER INFORMATION: Description of Artificial Sequence:blank

<400> SEQUENCE: 1
cgttcctcgg cgccgccggg gccccagagg gcagcggcag caacagcagc agcagcagca      60
gcgggagtgg agatggcggc ggcggcggct caggggggcg ggggcgggga gccccgtaga     120
accgaggggg tcggcccggg ggtcccgggg gaggtggaga tggtgaaggg gcagccgttc     180
gacgtgggcc cgcgctacac gcagttgcag tacatcggcg agggcgcgta cggcatggtc     240
agctcggcct atgaccacgt gcgcaagact cgcgtggcca tcaagaagat cagccccttc     300
gaacatcaga cctactgcca gcgcacgctc cgggagatcc agatcctgct gcgcttccgc     360
catgagaatg tcatcggcat ccgagacatt ctgcgggcgt ccaccctgga agccatgaga     420
gatgtctaca ttgtgcagga cctgatggag actgacctgt acaagttgct gaaaagccag     480
cagctgagca atgaccatat ctgctacttc ctctaccaga tcctgcgggg cctcaagtac     540
atccactccg ccaacgtgct ccaccgagat ctaaagccct ccaacctgct cagcaacacc     600
acctgcgacc ttaagatttg tgatttcggc ctggcccgga ttgccgatcc tgagcatgac     660
cacaccggct tcctgacgga gtatgtggct acgcgctggt accgggcccc agagatcatg     720
ctgaactcca agggctatac caagtccatc gacatctggt ctgtgggctg cattctggct     780
gagatgctct ctaaccggcc catcttccct ggcaagcact acctggatca gctcaaccac     840
attctgggca tcctgggctc cccatcccag gaggacctga attgtatcat caacatgaag     900
gcccgaaact acctacagtc tctgccctcc aagaccaagg tggcttgggc caagcttttc     960
cccaagtcag actccaaagc ccttgacctg ctggaccgga tgttaacctt taacccaat    1020 aaacggatca cagtggagga agcgctggct caccccctacc tggagcagta ctatgacccg    1080
acggatgagc cagtggccga ggagcccttc acctctgcca tggagctgga tgacctacct    1140
aaggagcggc tgaaggagct catcttccag gagacagcac gcttccagcc cggagtgctg    1200 gaggcccct agcccagaca gacatctctg caccctgggg cctggacctg cctcctgcct    1260
gcccctctcc cgccagactg ttagaaaatg gacactgtgc ccagcccgga ccttggcagc    1320
ccaggccggg gtggagcatg ggcctggcca cctctctcct ttgctgaggc ctccagcttc    1380
aggcaggcca aggccttctc ctcccacccg gccctcccca cggggcctcg ggagctcagg    1440
tggccccagt tcaatctccc gctgctgctg ctgctgcgcc cttaccttcc ccagcgtccc    1500
```

-continued

```
agtctctggc agttctggaa tggaagggtt ctggctgccc caacctgctg aagggcagag    1560
gtggagggtg gggggcgctg agtagggact cagggccatg cctgcccccc tcatctcatt    1620
caaaccccac cctagtttcc ctgaaggaac attccttagt ctcaagggct agcatccctg    1680
aggagccagg ccgggccgaa tcccctccct gtcaaagctg tcacttcgcg tgccctcgct    1740
gcttctgtgt gtggtgagca gaagtggagc tggggggcgt ggagagcccg cgcccctgc    1800 cacctccctg acccgtctaa tatataaata tagagatgtg tctatggctg aaaaaaaaaa    1860
aaaaaa    1866
```

<210> SEQ ID NO 2
<211> LENGTH: 1611
<212> TYPE: DNA
<213> ORGANISM: Homo sapiens
<220> FEATURE:
<223> OTHER INFORMATION: Description of Artificial Sequence:blank

<400> SEQUENCE: 2

```
acataatttc tggagccctg taccaacgtg tggccacata ttctgtcagg aaccctgtgt      60
gatcatggtc tggatctgca acacgggcca ggccaaagtc acagatcttg agatcacagg     120
tggtgttgag cagcaggcag gcaggcaatc ggtccgagtg gctgtcggct cttcagctct     180
ccgctcggcg tcttccttcc ctcccgtc agcgtcggcg gctgcaccgg cggcgggcag       240
tcctgcggga ggggcgacaa gagctgaggc gcggccgccg agcgtcgagc tcagcgcggc     300
ggaggcggcg gcggcccggc agccaacatg gcggcggcg cggcggcggg cgcgggcccg      360
gagatggtcc gcgggcaggt gttcgacgtg gggccgcgct acaccaacct ctcgtacatc     420
ggcgagggcg cctacggcat ggtgtgctct gcttatgata atgtcaacaa agttcgagta     480
gctatcaaga aaatcagccc ctttgagcac cagacctact gccagagaac cctgagggag     540
ataaaaatct tactgcgctt cagacatgag aacatcattg gaatcaatga cattattcga     600
gcaccaacca tcgagcaaat gaaagatgta tatatagtac aggacctcat ggaaacagat     660
ctttacaagc tcttgaagac acaacacctc agcaatgacc atatctgcta ttttctctac     720
cagatcctca gagggttaaa atatatccat tcagctaacg ttctgcaccg tgacctcaag     780
ccttccaacc tgctgctcaa caccacctgt gatctcaaga tctgtgactt tggcctggcc     840
cgtgttgcag atccagacca tgatcacaca gggttcctga cagaatatgt ggccacacgt     900
tggtacaggc tccagaaaat tatgttgaat tccaagggct acaccaagtc cattgatatt     960
tggtctgtag gctgcattct ggcagaaatg ctttccaaca ggcccatctt tccagggaag    1020
cattatcttg accagctgaa tcacattttg ggtattcttg gatccccatc acaagaagac    1080
ctgaattgta taataaattt aaaagctagg aactatttgc tttctcttcc acacaaaaat    1140
aaggtgccat ggaacaggct gttcccaaat gctgactcca agctctgga cttattggac     1200 aaaatgttga cattcaaccc acacaagagg attgaagtag aacaggctct ggcccaccca    1260
tatctggagc agtattacga cccgagtgac gagcccatcg ccgaagcacc attcaagttc    1320
gacatggaat tggatgactt gcctaaggaa aagctaaaag aactaatttt tgaagagact    1380
gctagattcc agccaggata cagatcttaa atttgtcagg caagggctc agaggactgg     1440 acgtgctcag acatcggtgt tcttcttccc agttcttgac ccctggtcct gtctccagcc    1500
cgtcttggct tatccacttt gactcctttg agccgtttgg aggggcggtt tctggtagtt    1560 gtggcttta tgctttcaaa gaatttcttc agtccagaga attcactggc c              1611
```

-continued

```
<210> SEQ ID NO 3
<211> LENGTH: 17
<212> TYPE: RNA
<213> ORGANISM: Artificial Sequence
<220> FEATURE:
<223> OTHER INFORMATION: Description of Artificial Sequence: synthesized
      antisense oligonucleotide

<400> SEQUENCE: 3
gccgccgccg ccgccau                                              17

<210> SEQ ID NO 4
<211> LENGTH: 17
<212> TYPE: DNA
<213> ORGANISM: Artificial Sequence
<220> FEATURE:
<223> OTHER INFORMATION: Description of Artificial Sequence: synthesized
      antisense oligonucleotide

<400> SEQUENCE: 4
gccgccgccg ccgccat                                              17
```